US008864735B2

(12) United States Patent
Sano et al.

(10) Patent No.: US 8,864,735 B2
(45) Date of Patent: Oct. 21, 2014

(54) BLOW-MOLDED PLASTIC INFUSION CONTAINER

(75) Inventors: Yoshihiko Sano, Osaka (JP); Hitoshi Futagawa, Osaka (JP); Toshihiro Kikuchi, Osaka (JP)

(73) Assignee: Nipro Corporation, Osaka (JP)

( * ) Notice: Subject to any disclaimer, the term of this patent is extended or adjusted under 35 U.S.C. 154(b) by 771 days.

(21) Appl. No.: 12/442,640

(22) PCT Filed: Sep. 25, 2007

(86) PCT No.: PCT/JP2007/068586
§ 371 (c)(1), (2), (4) Date: Mar. 24, 2009

(87) PCT Pub. No.: WO2008/041564
PCT Pub. Date: Apr. 10, 2008

(65) Prior Publication Data
US 2009/0270830 A1 Oct. 29, 2009

(30) Foreign Application Priority Data
Sep. 25, 2006 (JP) ................................ 2006-259797
Aug. 16, 2007 (JP) ................................ 2007-212093

(51) Int. Cl.
*B65D 6/00* (2006.01)
*B65D 25/10* (2006.01)
*A61B 19/00* (2006.01)
*B65D 1/02* (2006.01)
*A61J 1/05* (2006.01)
*B65D 23/00* (2006.01)

(52) U.S. Cl.
CPC ................ *B65D 1/0261* (2013.01); *A61J 1/05* (2013.01); *B65D 23/003* (2013.01)
USPC ........................... 604/403; 220/666; 220/751

(58) Field of Classification Search
USPC .......... 604/317, 403; 220/600, 604, 608, 610, 220/613, 631, 635, 666, 669, 675, 677, 751, 220/752
See application file for complete search history.

(56) References Cited

U.S. PATENT DOCUMENTS 3,926,341 A 12/1975 Lhoest
2007/0272705 A1 11/2007 Beine et al.

FOREIGN PATENT DOCUMENTS

DE 103 42 742 A1 5/2005
JP 2002-80021 A 3/2002
JP 2002-282335 A 10/2002
JP 2004-175406 A 6/2004

OTHER PUBLICATIONS

English translation of JP 2002282335 A to Nakamura.*
English abstract and drawings for JP 2002-080021 A to Nakamura.*

* cited by examiner

*Primary Examiner* — Melanie Hand
(74) *Attorney, Agent, or Firm* — Birch, Stewart, Kolasch & Birch, LLP

(57) ABSTRACT

A bottle-type blow-molded plastic infusion container that can be set in an upright position. When liquid is discharged from the container, almost no dead space occurs in shoulder and bottom portions (required amount of air to be placed in the container to remove residual liquid is less). The blow-molded container has a mouth section (1), a neck section (2), the shoulder section (3), a barrel section (4), and the bottom section (5). The barrel section (4) has a pair of broad side faces (41, 41) and a pair of narrow side faces (42, 42). The bottom section (5) is formed in a shape symmetrical about a longitudinal axis of the bottom section (5) and bent inward in a V shape. Further, the shoulder section (3) has a pair of broad side faces (31, 31) and a pair of narrow side faces (32, 32). In the narrow side faces (32, 32) are formed grooves (33, 33) symmetrical about a longitudinal axis and bent inward in a V shape.

20 Claims, 17 Drawing Sheets

BLOW-MOLDED PLASTIC INFUSION CONTAINER

TECHNICAL FIELD

The present invention relates to a blow-molded plastic infusion container for storing an infusion solution or dextrose solution for use in intravenous drip therapy or the like.

BACKGROUND ART

There are what are known as the plastic infusion containers; a bag type made of a plastic sheet and a bottle type produced by blow-molding.

The bottle type infusion containers have the advantage of being able to stand upright. However, such bottle type infusion containers are formed by blow-molding, causing problems in flexibility. Thus, the blow-molded containers can not be sufficiently flattened under pressure by the discharge of the drug solution, causing excessive amounts of the drug solution to remain in the container. For this reason, some measures taken in the prior art are those such as, for example, a method of inserting an air needle into a rubber stopper of the container, in which the inside and the outside of the container are fluid-communicated with each other through said air needle to allow the air to flow into the container in response to the outflow of the drug solution when performing the transfusion of the drug solution at a constant flow rate, or use of an infusion container filled with the drug solution of less than the container capacity to increase an amount of air or gas to be contained in the container.

However, the method of insertion of the air needle into the rubber stopper of the container has a disadvantage for working since it takes a lot of trouble for insertion of the air needle and since it requires extreme care to prevent it from being contaminated by harmful bacteria. Further, the method of increasing the content of the gas such as air in the container is disadvantageous in that the container increases in size with reserving the space for air to be charged therein. In addition, the method, when performed by the use of an infusion pump, necessitates additional human hands and devices since it is necessary to monitor and prevent the introduction of excess air into the blood vessel of the patient because of a fluid level sensor failure.

On the other hand, the bag type containers have the advantage of being able to exclude the residual liquid from the container since all parts except the mouth of the container are made of a flexible plastic sheet and thus they are easily flattened by themselves in response to the outflow of the drug solution without use of any air needle. However, such bag type containers have a disadvantage for performing the infusion since they can not be held upright because of the material and shape of the container.

As a result, there have been proposed bottle type infusion containers capable of being kept upright, which are adapted to be easily flattened to reduce the air quantity and residual liquid, such as an infusion container provided with four grooves parallel to the bottom in places in wide sidewalls of the barrel (patent document 1), and an infusion container provided with mountain fold lines (5, 5) passing longitudinally through the center of both sidewalls of the container barrel, said mountain fold lines bifurcating at the position near the bottom and extending from said position to both corners of sidewalls near the bottom, wherein the barrel is further provided with valley fold lines (5*a*, 5*a*) on both sides of each mountain fold line (5, 5), and a valley fold line (7) passing through the side walls and a front wall of the container barrel in parallel with the bottom to communicate the valley fold lines with each other (patent document 2).

However, the infusion container of patent document 1 possesses insufficient flattening of the shoulder and bottom, and thus there is dissatisfaction with a large amount of air to be injected. The infusion container of patent document 2 has been somewhat improved in flattening property, but it is insufficient in flattening of the shoulder and bottom, in particular, flattening of the shoulder, which therefore causes dissatisfaction because of a large amount of air to be injected.

Patent document 1: JP, H06-000114Y

Patent document 2: JP, P2002-282335A

DISCLOSURE OF INVENTION

Problems to be Solved by the Invention

The present invention has been made on the aforesaid circumstances and is aimed at providing a blow-molded plastic infusion container capable of being kept upright, which has almost no dead space in a shoulder and in a bottom at the time of discharge of liquid (Accordingly, it is small in amount of air to be injected for removal of the residual liquid).

Another object of the present invention is to provide an infusion container capable of being flattened with ease so as not to take up much space as well as increasing convenience for disposal of containers after injection of the drug solution.

Means for Solving the Problems

According to the present invention, there is provided a blow-molded plastic infusion container having a mouth, a neck, a shoulder, a barrel and a bottom, characterized in that the barrel has a pair of wide sidewalls and a pair of narrow sidewalls, and that the bottom is formed into a V-shape bent inwardly and symmetrically with respect to the long axis of the bottom.

Here the shoulder has a pair of wide sidewalls and a pair of narrow sidewalls, of which the narrow sidewalls may be provided with groove portions of a V-shape bent inwardly and symmetrically with respect to the long axis of the bottom. Further, the bottom and shoulder may be provided at the curved portions thereof with inwardly foldable fold lines, for example, by hot press molding.

The narrow sidewalls of the barrel may be provided with fold lines, which are outwardly foldable and symmetrical to the longitudinal axis of the barrel, for example, by hot press molding.

Also, the fold lines may be formed, for example, by making an internal pressure of the blow-molding die negative. In the present invention, the term “inward” means an internal side of the container, while the term “outward” means an external side of the container.

Although the present invention has been generally explained as above, further understanding will be given by making reference to some specific examples. However, these examples are given only by way of illustration and are not considered to be limited examples unless otherwise specified.

Effects of the Invention

According to the present invention, the following advantageous effects are produced: Since the infusion container of the present invention is so blow-molded that a barrel has a pair of wide sidewalls and a pair of narrow sidewalls, the narrow sidewalls are made into a thin-walled section as compared with other parts, and thus the barrel is apt to be flattened in the direction of the short axis of the barrel. Further, since the bottom is formed into a V-shape bent inwardly and symmetrically with respect to the long axis of the bottom, i.e., since the external side of the bottom is formed by blow-molding so as to be concaved longitudinally like a V-shaped groove, the curved sections between the wide sidewalls and V-shaped portions are made relatively thin, allowing the inner wall surfaces of the wide sidewalls and the inner wall surfaces of the V-shaped portions to come into closely contact with one another by discharge of the liquid, resulting in almost no residual liquid in the bottom of the container.

Further, the shoulder has a pair of wide sidewalls and a pair of narrow sidewalls, of which the narrow sidewalls may be provided with groove portions of a V-shape bent inwardly and symmetrically with respect to the long axis of the bottom. In this case, curved portions between the narrow sidewalls of the shoulder and the grooves are relatively made thin as compared with other portions, allowing the inner wall surfaces of the wide sidewalls and the V-shaped portions to come into contact with one another by discharging the liquid, thereby considerably reducing the amount of the residual liquid in the shoulder. In addition, when the bottom and the shoulder are provided in the curved portions thereof with fold lines, they become more easily foldable in the short axis direction. Further, when the barrel is provided in the narrow sidewalls thereof with fold lines foldable outward and symmetric to the longitudinal axis, it becomes more easily foldable in the short axis direction. When the whole container is apt to be foldable under pressure, it is possible to decrease the volume of the containers at the time of throwing out the containers, thus making it possible to reduce the costs incurred during waste disposal.

In the conventional bottle, the amount of air to be injected into the bottle for removal of the residual liquid is determined by a volume of unfolded portions of the bottle under the flattened conditions of the bottle. In contrast therewith, the infusion container of the present invention makes it possible to considerably reduce the amount of air to be injected as compared with the conventional containers. Because, the infusion container of the present invention has a bottom with a configuration of a V-shape bent inwardly and symmetrically with respect to the long axis of the bottom, and a shoulder with V-shaped grooves, allowing the wide sidewalls of both the barrel and shoulder to respectively move toward the V-shaped wall of the bottom and the V-shaped grooves of the shoulder at the time of discharge of the solution, resulting in almost no space between the wide sidewalls and the V-shaped wall of the bottom and between the wide sidewalls and the V-shaped grooves of the shoulder.

Additionally, the V-shaped grooves formed in the shoulder are allowed to telescope into a part adjacent to the scarcely foldable neck to fill the aforesaid adjacent part that may create a dead space, thus making it possible to reduce the injection volume of air by just that much.

In case that the bottom is so designed as to have a grounding portion with edge lines linearized in the direction parallel to the long axis of the bottom, the edge portions of the grounding portion which become folds are subjected to stresses in the same direction, resulting in improvement in flexibility of the edge portions. As a result, the bottom is further reduced in the dead space, resulting in almost no residual liquid in the bottom even after sterilization.

EXPLANATION OF REFERENCE SYMBOLS

Figure 1:
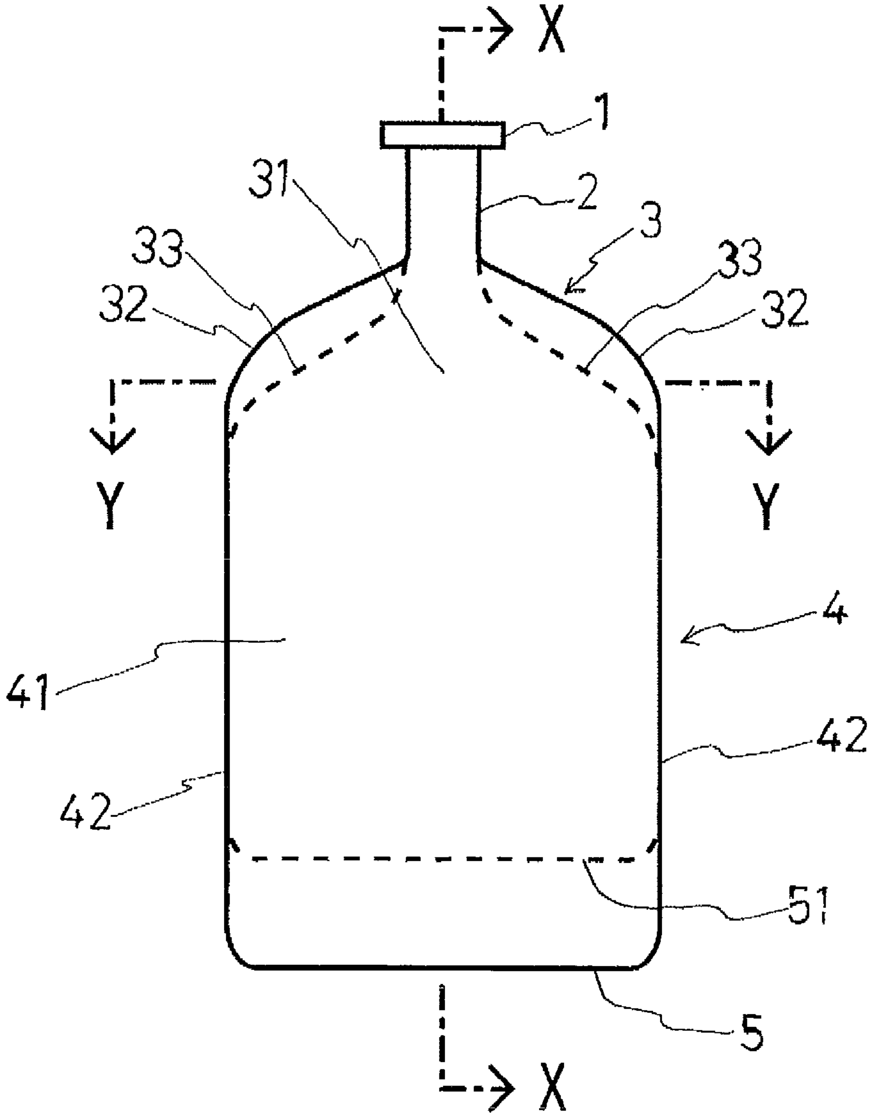
FIG. 1 is a front view of an infusion container illustrating example 1 of the present invention.

1 mouth
2 neck
3 shoulder
31 wide sidewall
32 narrow sidewall
33 groove
4 barrel
41 wide sidewall
42 narrow sidewall
5 bottom
51 V-shaped portion
101 mouth
102 neck
103 shoulder
131, 131' wide sidewall
132, 132' narrow sidewall
133, 133' groove
134 curved portion
104 barrel
141, 141' wide sidewall
142, 142' narrow sidewall
105 bottom
151 V-shaped portion
152, 152' edge line of a grounding portion that comes in contact with a supporting surface of any supporting means when the container is put on the supporting means
153, 153' curved portion
154, 154' narrow sidewall near the bottom
100 infusion container of example 5
200 infusion container of example 6
262, 262' linearized ridge-like line in a curved portion of shoulder
300 infusion container of example 7
305 bottom

352, 352' edge line of a grounding portion that comes in contact with a supporting surface of any supporting means when the container is put on the supporting means

BEST MODE FOR CARRYING OUT THE INVENTION

The blow-molded plastic infusion container of the present invention is a container having a mouth, a neck, a shoulder, a barrel and a bottom and is characterized in that the barrel has a pair of wide sidewalls and a pair of narrow sidewalls and that the bottom is formed into a V-shape bent inwardly and symmetrically with respect to the long axis of the bottom. The shoulder has a pair of wide sidewalls and a pair of narrow sidewalls, of which the narrow sidewalls are formed into a V-shape bent into inward and symmetric to the long axis. Further, the bottom is so formed that edge lines 152 of the grounding portion extend linearly in the direction of the long axis of the bottom and are parallel to the long axis of the bottom. Also, the shoulder is so formed that the ridge lines of the shoulder among the curved portions of the shoulder extend linearly in the long axis direction and are parallel to the long axis of the bottom.

Example 1

Firstly, example 1 of the present invention will be explained with reference to FIG. 1 to FIG. 5.

Figure 2:
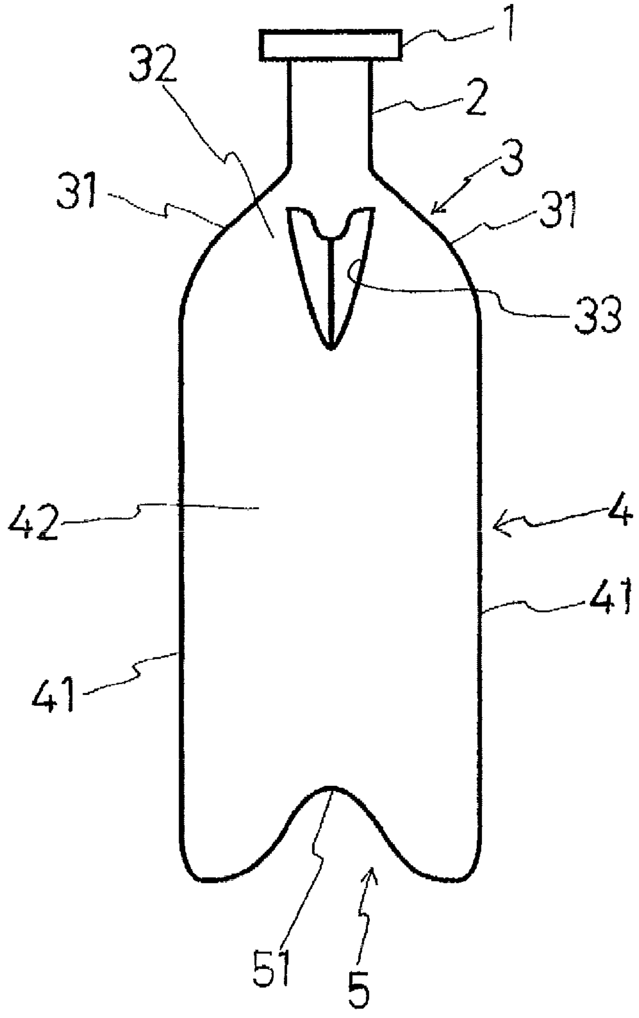
FIG. 2 is a side view of the container shown in FIG. 1.
Figure 3:
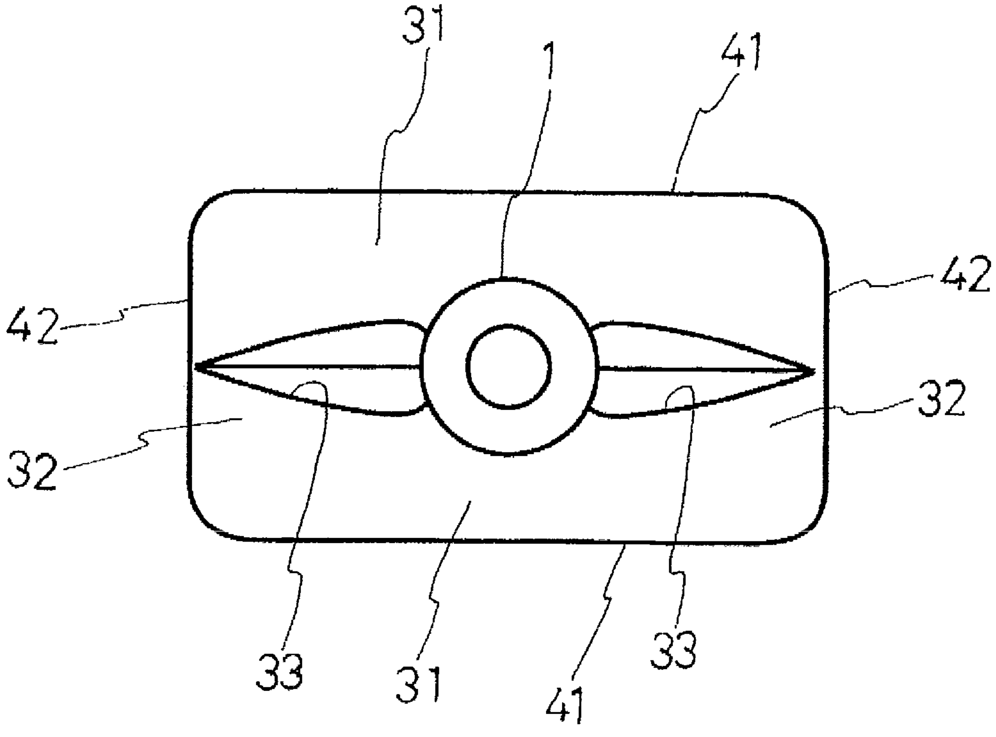
FIG. 3 is a plan view of the container shown in FIG. 1.
Figure 4:
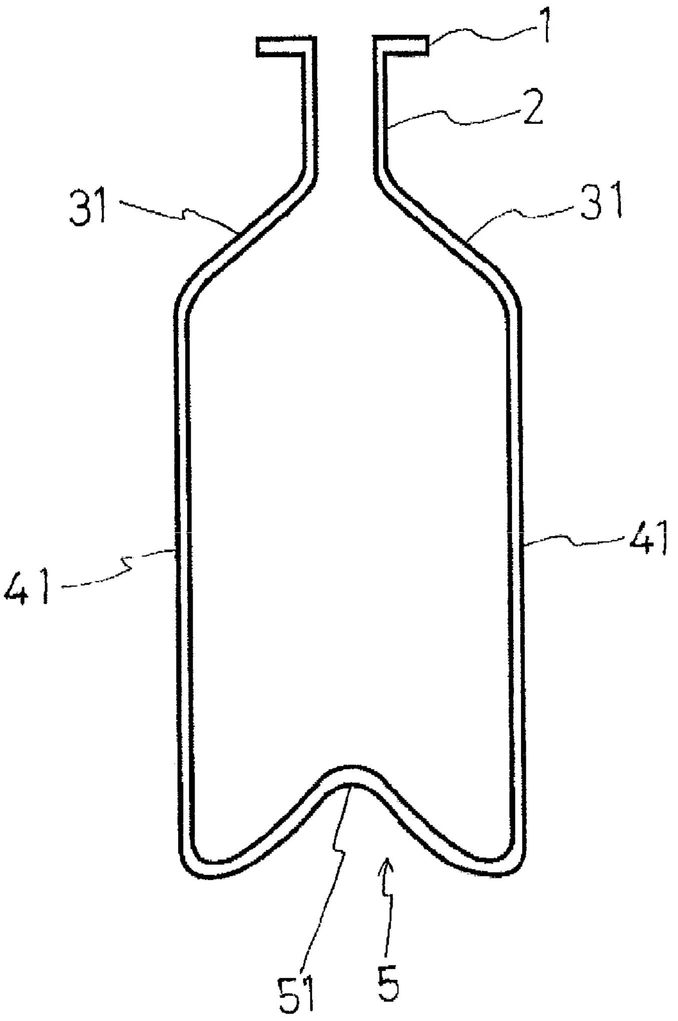
FIG. 4 is a cross-section view of the container taken along the line X-X in FIG. 1.
Figure 5:
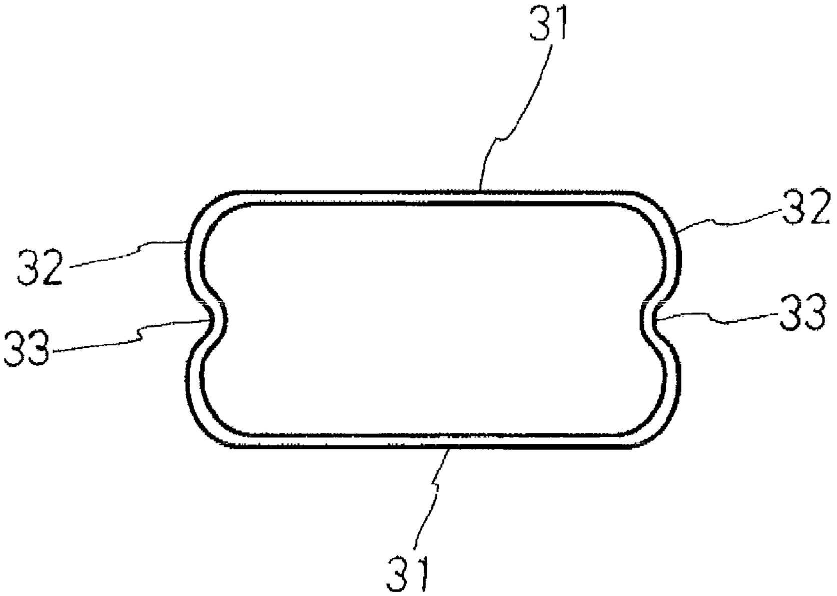
FIG. 5 is a cross-section view of the container taken along the line Y-Y in FIG. 1.

FIG. 1 is a front view of an infusion container illustrating example 1 of the present invention; FIG. 2 is a side view of the container shown in FIG. 1; FIG. 3 is a plan view of the container shown in FIG. 1; FIG. 4 is a cross-section view of the container taken along the line X-X in FIG. 1; FIG. 5 is a cross-section view of the container taken along the line Y-Y in FIG. 1.

As shown in FIGS. 1-5, the infusion container of example 1 is a blow-molded container having a mouth 1, a neck 2, a shoulder 3, a barrel 4 and a bottom 5. The barrel 4 has a pair of wide sidewalls 41, 41 and a pair of narrow sidewalls 42, 42. The bottom 5 is formed into a V-shape bent inwardly and symmetrically with respect to the long axis of the bottom. The shoulder 3 also has a pair of wide sidewalls 31, 31 and a pair of narrow sidewalls 32, 32, of which the narrow sidewalls 32, 32 are respectively provided with an inwardly-projecting V-shaped groove 33, 33 which is symmetric to the long axis. As shown in FIG. 2, the V-shaped groove 33 has a wide end and a pointed end, the wide end joins and extends from the neck 2, and the pointed end is positioned away from the neck 2 toward the barrel 4. Further, the curved portions of the bottom 5 and shoulder 3 are respectively provided with fold lines (not shown in the figures). Also the narrow sidewalls 42, 42 of the barrel 4 are provided with fold lines (not shown in the figure) which are foldable outwardly and symmetric to the long axis.

In case of the blow-molded container, the wide sidewalls 31, 41 of the shoulder 3 and barrel 4 are generally symmetric to the short axis, while the narrow sidewalls 32, 42 of the shoulder 3 and barrel 4 are symmetric to the long axis. It is to be noted that means for hanging the infusion container has been omitted from the drawings.

By the above structure, the infusion container of example 1 is so formed that curved portions between the V-shaped portion 51 of the bottom 5 and the wide sidewalls 41, 41 of the barrel 4 and the curved portions between the grooves 33 of the shoulder 3 and the narrow sidewalls 32, 32 of the shoulder 3 are relatively thin compared with the wide sidewalls. Thus, this structure allows the container to be crushed flatly along with discharge of the solution from the container, causing the wide sidewalls 41, 31 of both the barrel 4 and shoulder 3 to be respectively moved toward the V-shaped portion 51 of the bottom 5 and the groove 33 of the shoulder, so that there remains almost no space between the wide sidewalls 41 and the V-shaped portions 51 and between the wide sidewalls 31 and the grooves 33. Accordingly, the container is considerably decreased in dead space, thus making it possible to considerably reduce the injection volume of air as compared with the conventional infusion containers. Further, the bottom 5 and the shoulder 3 are so constructed as to be easily foldable in the short axis direction along the fold lines, so that the whole container becomes easily foldable in the short axis direction along with the discharge of liquid. In addition, the container is constructed to allow the barrel 4 to be easily folded in the short axis direction along the fold lines, so that the whole container becomes more easily foldable in the short axis direction along with the discharge of liquid.

The V-shaped grooves 33 in the shoulder 3 are allowed to telescope into a part adjacent to the non-collapsible neck, thereby filling the aforesaid adjacent part that creates a dead space, thus making it possible to further reduce the dead space.

Example 2

Secondly, the present invention will be explained on example 2 with reference to FIG. 6 to FIG. 10.

Figure 6:
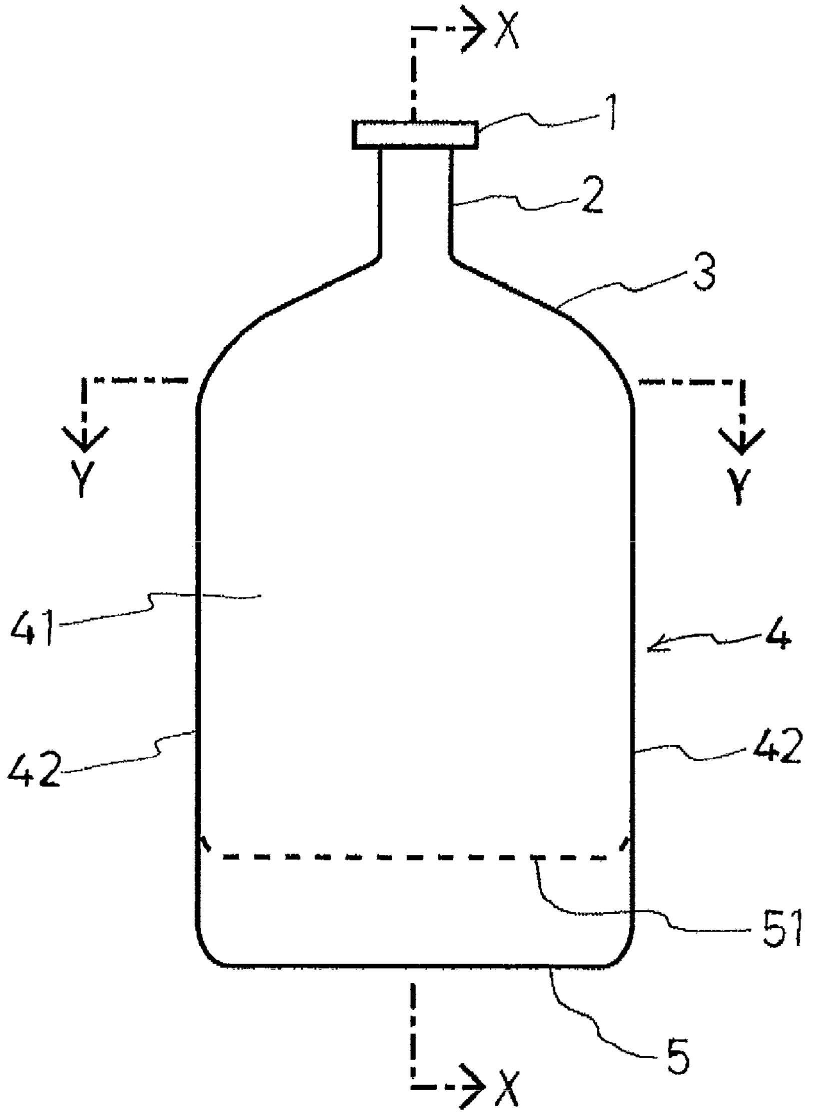
FIG. 6 is a front view of an infusion container illustrating example 2 of the present invention.
Figure 7:
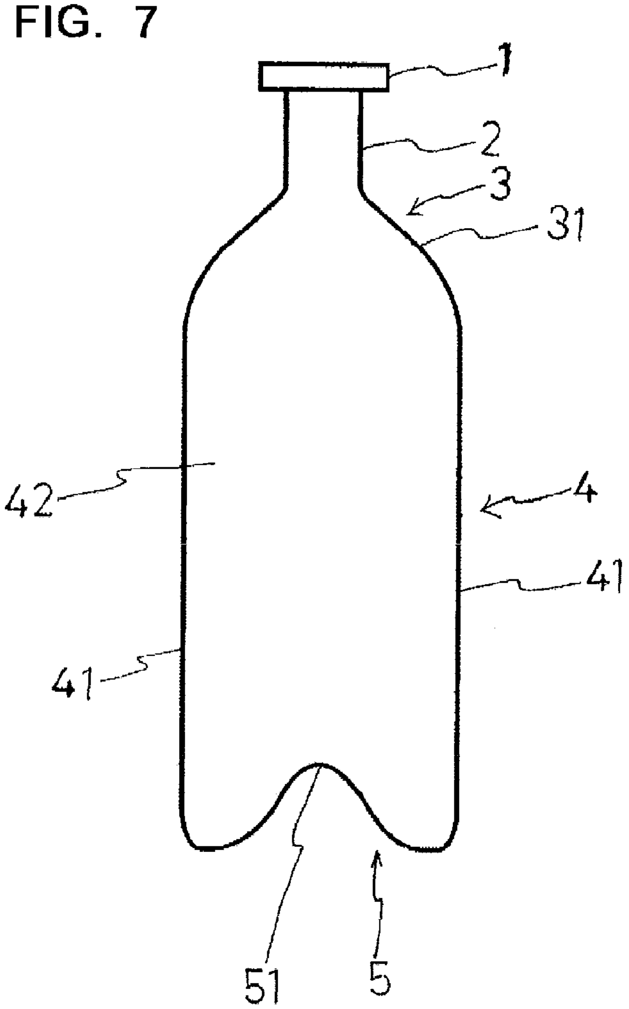
FIG. 7 is a side view of the container shown in FIG. 6.
Figure 8:
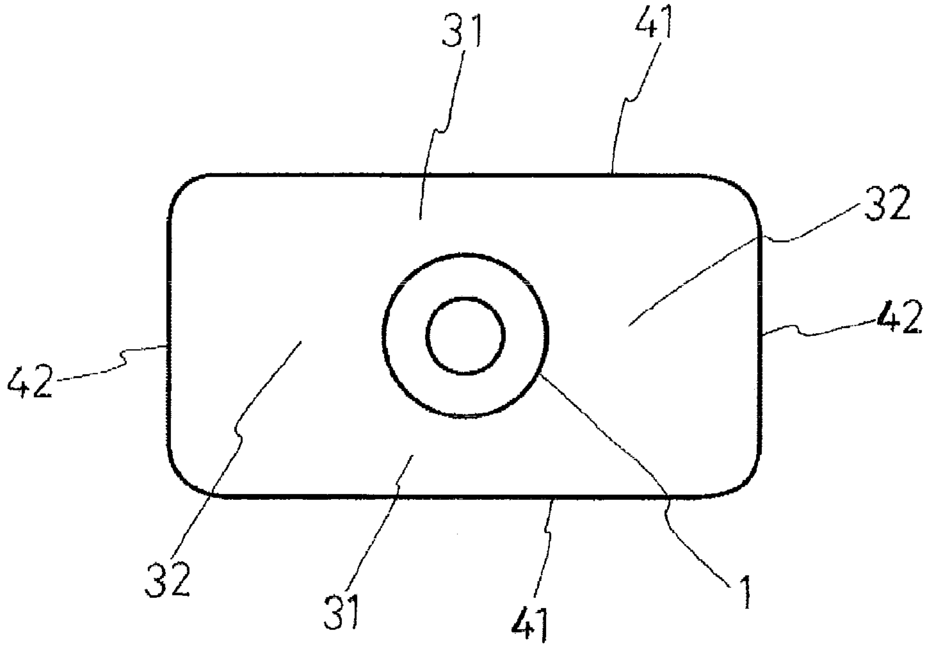
FIG. 8 is a plan view of the container shown in FIG. 6.
Figure 9:
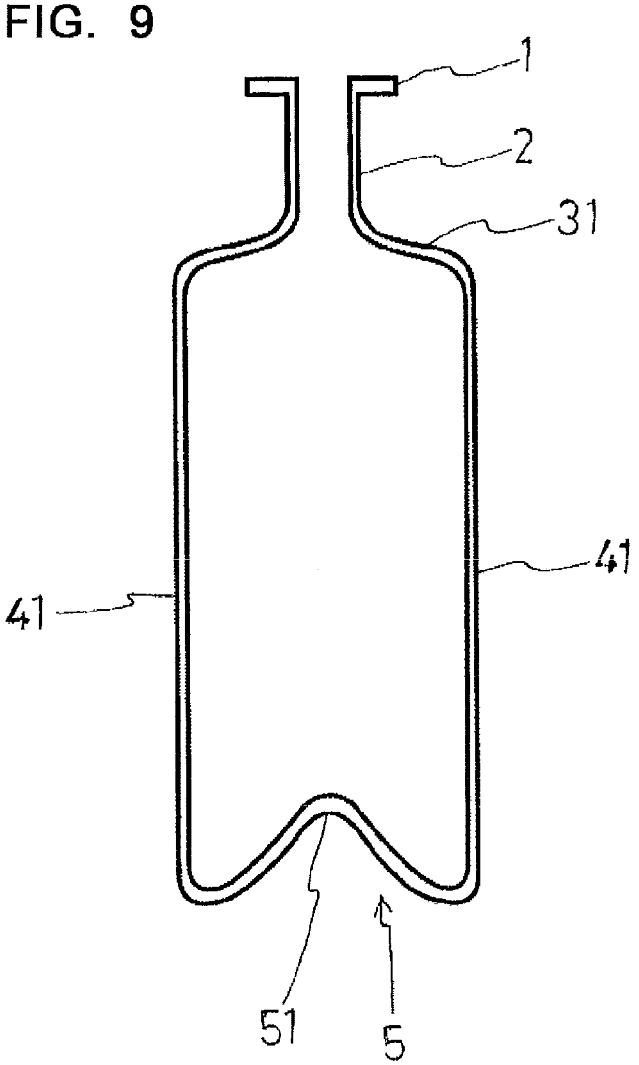
FIG. 9 is a cross-section view of the container taken along the line X-X in FIG. 6.
Figure 10:
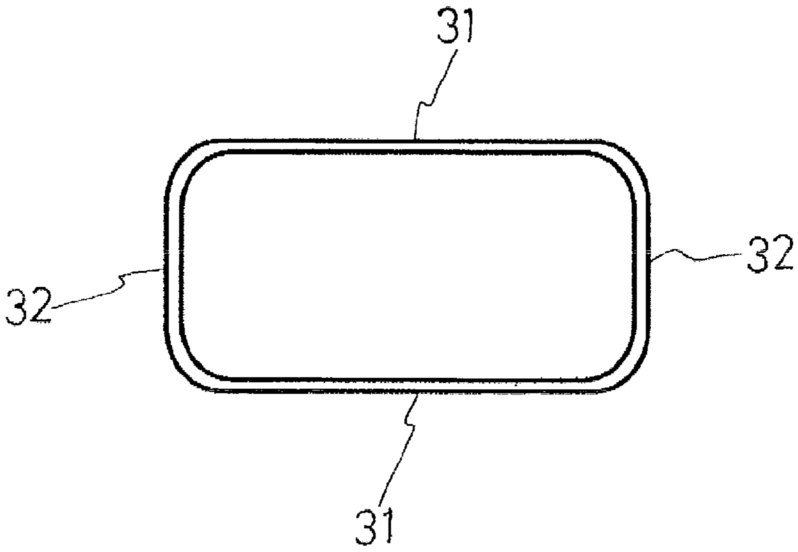
FIG. 10 is a cross-section view of the container taken along the line Y-Y in FIG. 6.

FIG. 6 is a front view of an infusion container according to example 2 of the present invention; FIG. 7 is a side view of the container shown in FIG. 6; FIG. 8 is a plan view of the container shown in FIG. 6; FIG. 9 is a cross-section view of the container along the line X-X in FIG. 6; and FIG. 10 is a cross-section view of the container along the line Y-Y in FIG. 6.

As shown in FIGS. 6-10, the infusion container of example 2 is a container having a mouth 1, a neck 2, a shoulder 3, a barrel 4 and a bottom 5. The barrel 4 has a pair of wide sidewalls 41, 41 and a pair of narrow sidewalls 42, 42. The bottom 5 is formed into a V-shape which is bent inwardly and symmetrically with respect to the long axis of the bottom 5. Also, the shoulder 3 has a pair of wide sidewalls 31, 31 and a pair of narrow sidewalls 32, 32, among which the narrow sidewalls 32, 32 of the shoulder 3 are respectively provided with fold lines 321, 321 which are foldable outwardly and symmetrically with respect to the long axis. In addition, the curved portions of bottom 5 are provided with fold lines (not shown in the figures) by hot pressing, and the narrow sidewalls 42, 42 of the barrel (4) are provided with fold lines (not shown in the figures) which are foldable outwardly and symmetrically with respect to the long axis, by hot pressing.

Since the curved portions of the bottom 5 (i.e., a bottom part of the V-shaped portion 51 and the curved portions between the wide sidewalls 41 of the barrel 4 and the V-shaped portion 51) are relatively thinned and since the bottom 5 is so formed as to be easily folded along the curved portion thereof in the short axis direction, the whole container is apt to be easily crushed flatly in the short axis direction by discharge of the solution. In addition, when being crushed flatly, the container becomes the condition of having almost no space between the V-shaped portion 51 and the wide sidewalls because of the movement of the wide sidewalls 41, 41 of the barrel 4 toward the V-shaped portion 51 of the bottom 5 along with discharge of the solution. Further, since the narrow sidewalls 32, 32 of the shoulder 3 and the bottom 5 are so formed as to be easily folded in the direction of the short axis along the fold lines, the whole container is easily crushed flatly in the direction of the short axis by discharge of the solution. In addition, the barrel 4 is designed so as to be easily folded in the direction of the short axis along the fold lines, so that the whole container is more easily crushed flatly in the direction of the short axis by discharge of the solution.

Example 5 will be explained using FIGS. 12-16, and explanation on example 6 will be made using FIGS. 17 and 18, and explanation on example 7 will be made using FIGS. 19 and 20.

Figure 12:
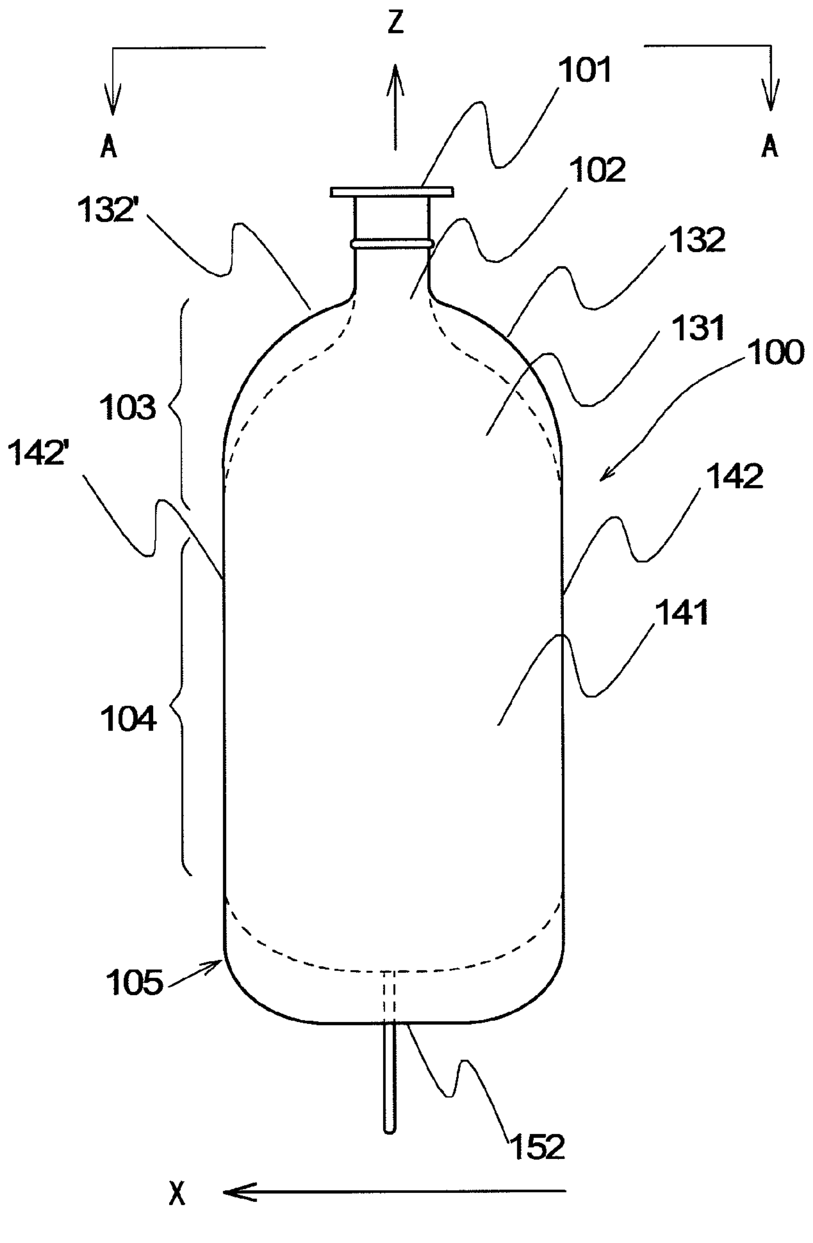
FIG. 12 is a front view of an infusion container illustrating example 5 of the present invention.
Figure 13:
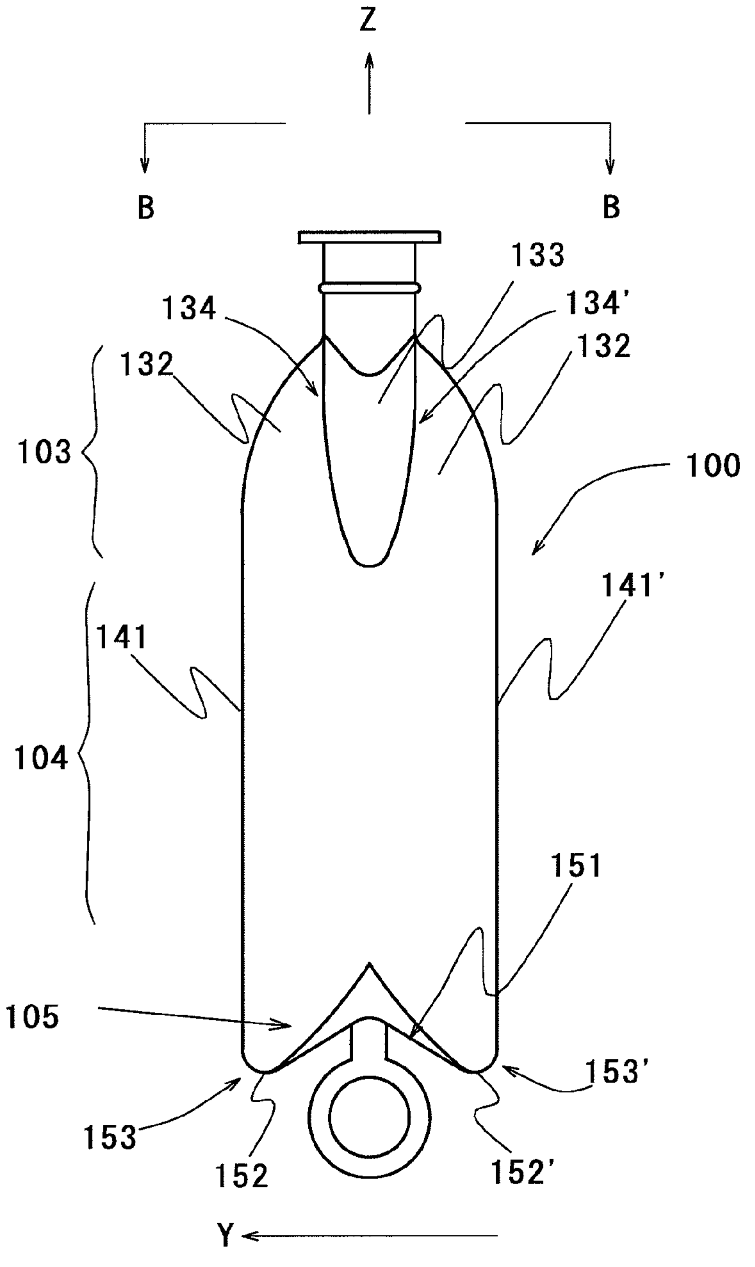
FIG. 13 is a side view of the container shown in FIG. 12.
Figure 14:
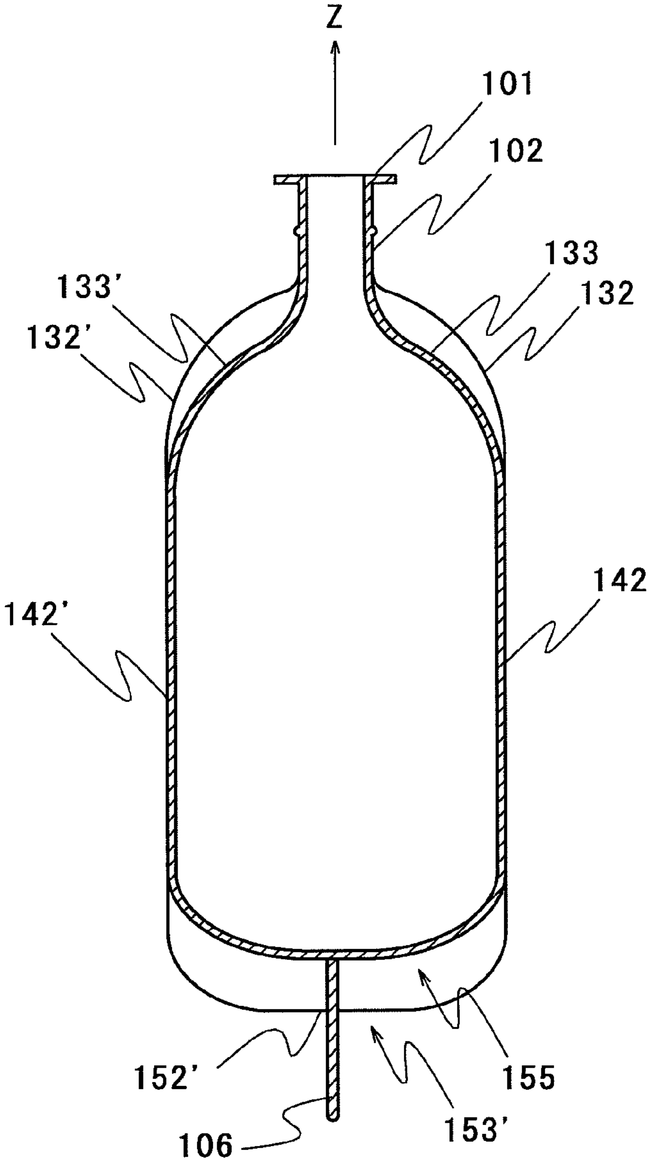
FIG. 14 is a cross-section view of the container taken along the line A-A in FIG. 12.
Figure 15:
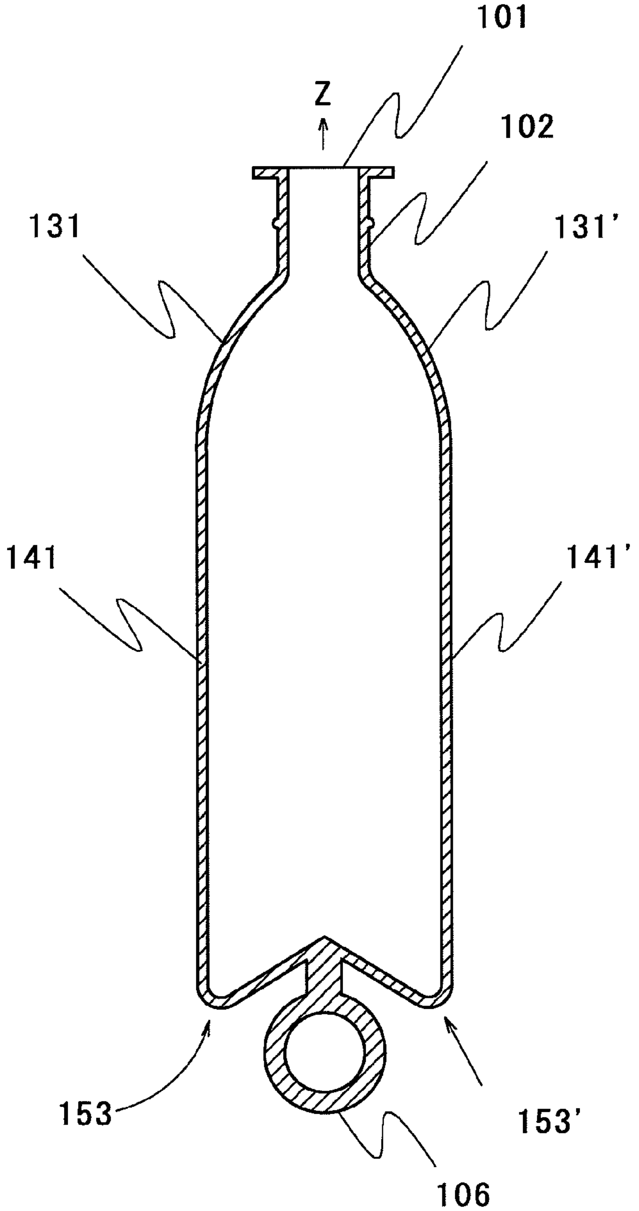
FIG. 15 is a cross-section view of the container taken along the line B-B in FIG. 13.
Figure 16:
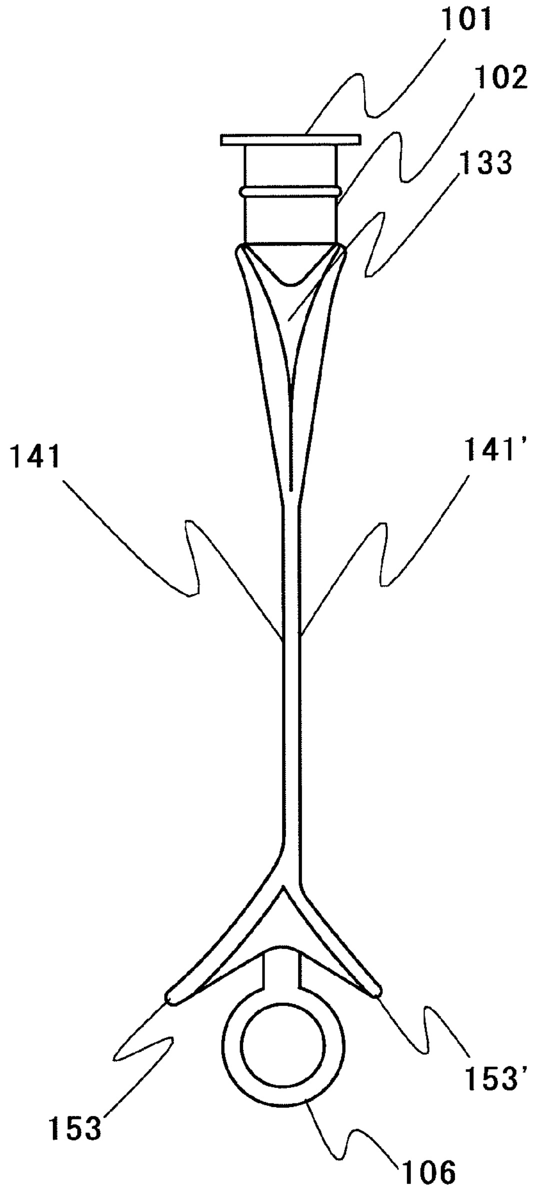
FIG. 16 is a schematic diagram illustrating a folded state of the container taken shown in FIG. 14.

FIG. 12 is a front view of an infusion container 100 illustrating example 5, which is one illustrative example of the present invention; FIG. 13 is a side view of the infusion container shown in FIG. 12; FIG. 14 is a cross-section view of the infusion container taken along the line A-A in FIG. 12; FIG. 15 is a cross-section view of the infusion container taken along the line B-B in FIG. 13; FIG. 16 is a schematic diagram showing the flattened state of the infusion container shown in FIG. 12; FIG. 17 is a front view of an infusion container 200 according to example 6 of the present invention; FIG. 18 is a side view of the infusion container shown in FIG. 17; FIG. 19 is a front view of an infusion container 300 according to example 7 of the present invention; and FIG. 20 is a side view of the infusion container shown in FIG. 19.

As shown in FIGS. 12-13, the infusion container 100 of example 5 is a blow-molded container having a mouth 101, a neck 102, a shoulder 103, a barrel 104 and a bottom 105. The barrel 104 has a pair of wide sidewalls 141, 141' and a pair of narrow sidewalls 142, 142'. The bottom 105 is formed into a V-shape bent inwardly and symmetrically with respect to the long axis of the bottom 105 so as to have a grounding portion with edge lines 152 that extend linearly in the direction of the long axis of the bottom. Also, bottom in parallel with the long axis of the bottom. Also, the shoulder 103 has a pair of wide sidewalls 131, 131' and a pair of narrow sidewalls 132, 132', among which the narrow sidewalls 132, 132' are respectively provided with groove 133, 133' of a V-shape bent inwardly and symmetrically with respect to the long axis. In case of blow-molding, generally the wide sidewalls 131, 141 of the shoulder 103 and barrel 104 are symmetric to the short axis Y, while the narrow sidewalls 132, 142 of the shoulder 103 and barrel 104 are symmetric to the long axis X. Additionally, reference symbol 106 denotes hanger means for hanging the infusion container.

Because of the above construction, the infusion container of example 5 is thinned at curved portions 153, 153' between the V-shaped portion 151 of the bottom 105 and the wide sidewalls 141, 141' of the barrel 104, and at curved portions 134, 134' between the grooves 133 of the shoulder 103 and the narrow sidewalls 132 of the shoulder 103, and the curved portions 153, 153' are subjected to stress in the same direction when the container is crushed flatly. Thus, the container is easily crushed flatly by discharge of the solution. In that case, the wide sidewalls 141 of the barrel 104 and the wide sidewall portions 131 of the shoulder 103 are respectively moved toward the V-shaped portion 151 of the bottom 106 and toward the grooves 133 of the shoulder, so that there remain almost no space between the wide sidewall portion and the V-shaped bottom wall portion 151 of the bottom 105 and between the wide sidewalls 131 and the grooves 133, thus making it possible to substantially reduce both the dead space and the air-injection amount as compared with the conventional ones. When the infusion container of example 5 is flattened as shown in FIG. 16, the V-shaped groove portions 133 of the shoulder 103 are allowed to telescope into a part adjacent to the scarcely foldable neck to fill the aforesaid adjacent part that may create a dead space, thus making it possible to reduce the injection volume of air.

Further, the infusion container of example 5 has a V-shaped recess 155 curved at both sides near the narrow sidewalls 142, 142' in the direction of the mouth, as shown in FIG. 14. The infusion container of example 5 is provided in the grounding portion with a pair of edge lines 152, 152' substantially parallel to the V-shaped recess 155, as shown in FIG. 14. The bottom 105 is formed into a configuration symmetrical with respect to the longitudinal axis Z of the container as shown in FIG. 15 which is a longitudinal sectional view of the infusion container along the line cutting the wide sidewalls in pair.

Figure 17:
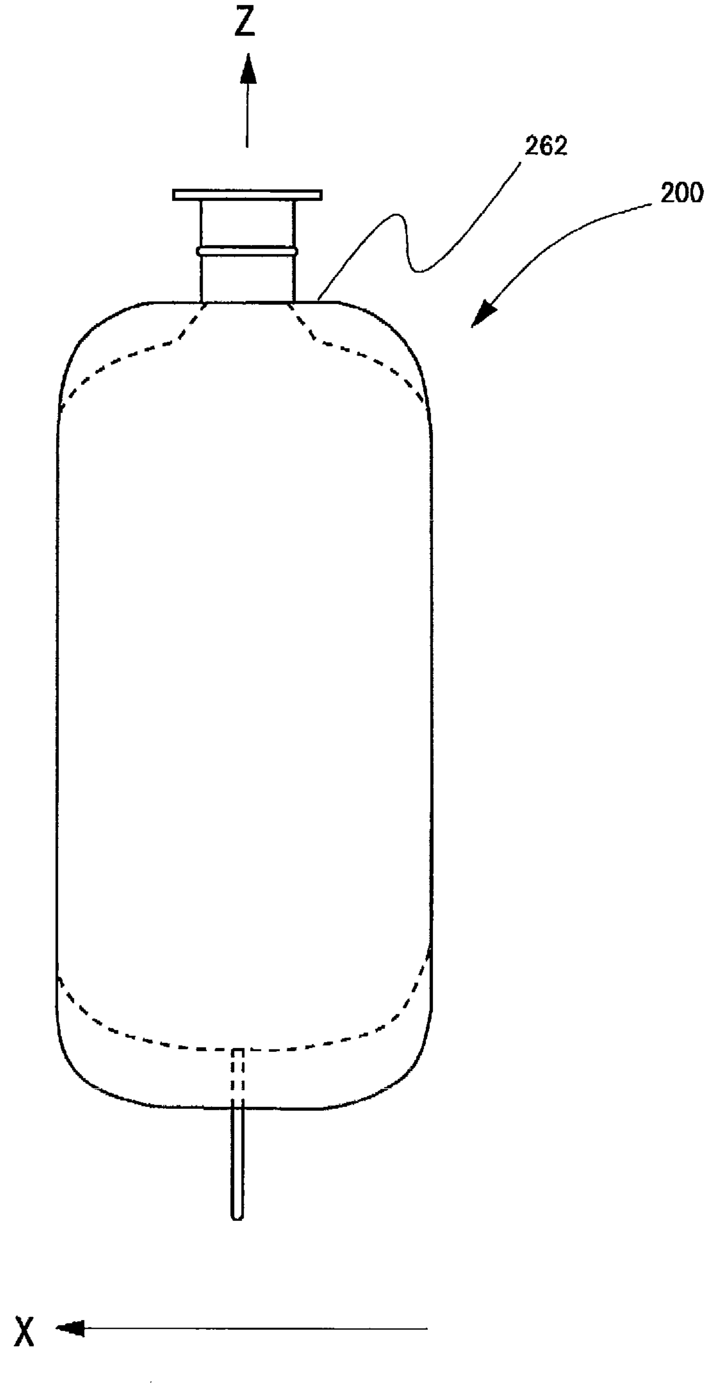
FIG. 17 is a front view of an infusion container illustrating example 6 of the present invention.
Figure 18:
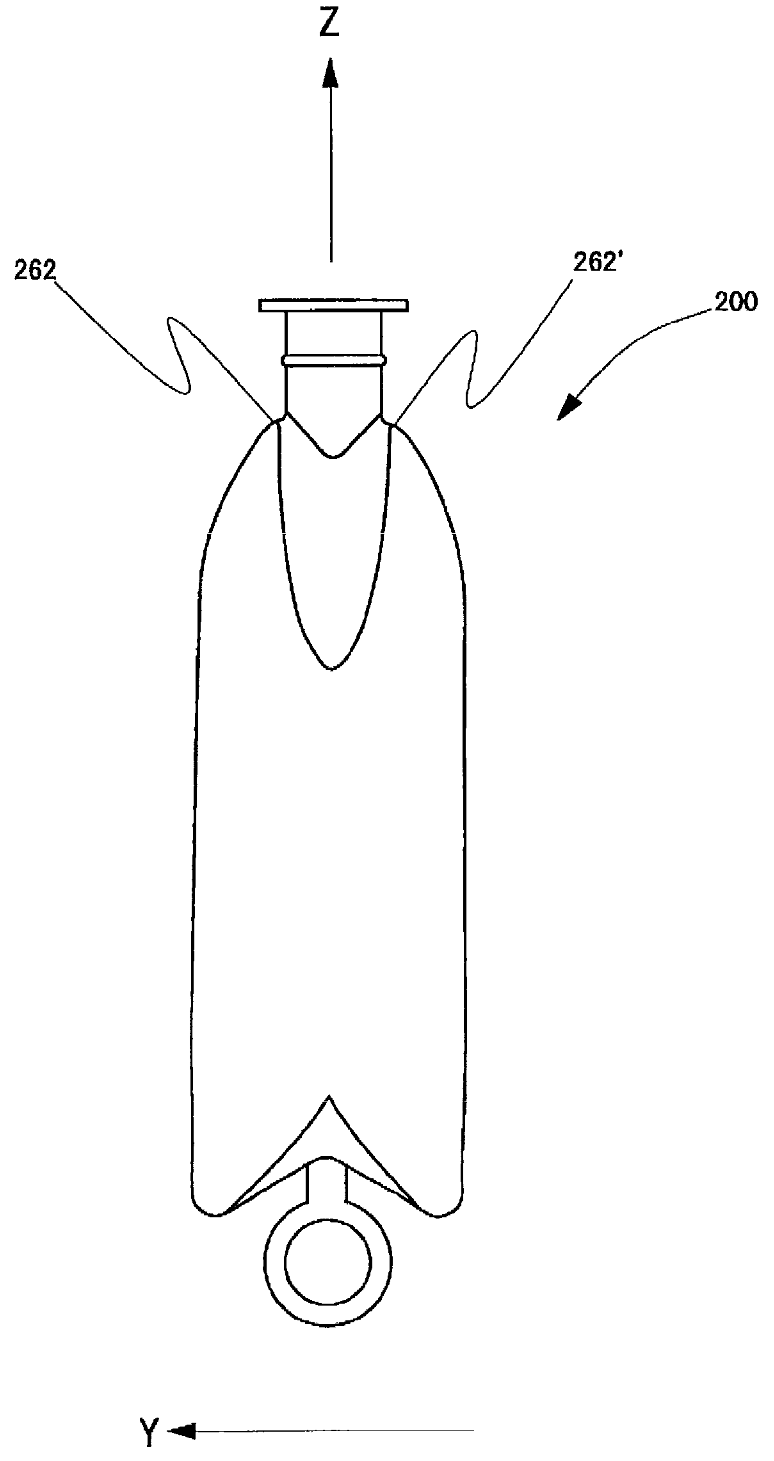
FIG. 18 is a side view of the container shown in FIG. 17.

The infusion container of example 6 differs from the infusion container of example 5 in that ridge-like lines located at the top portions in curved portions of the shoulder are formed into straight lines extending in parallel with the long axis of the bottom in the direction of the long axis of the bottom, as shown in FIGS. 17 and 18.

Figure 19:
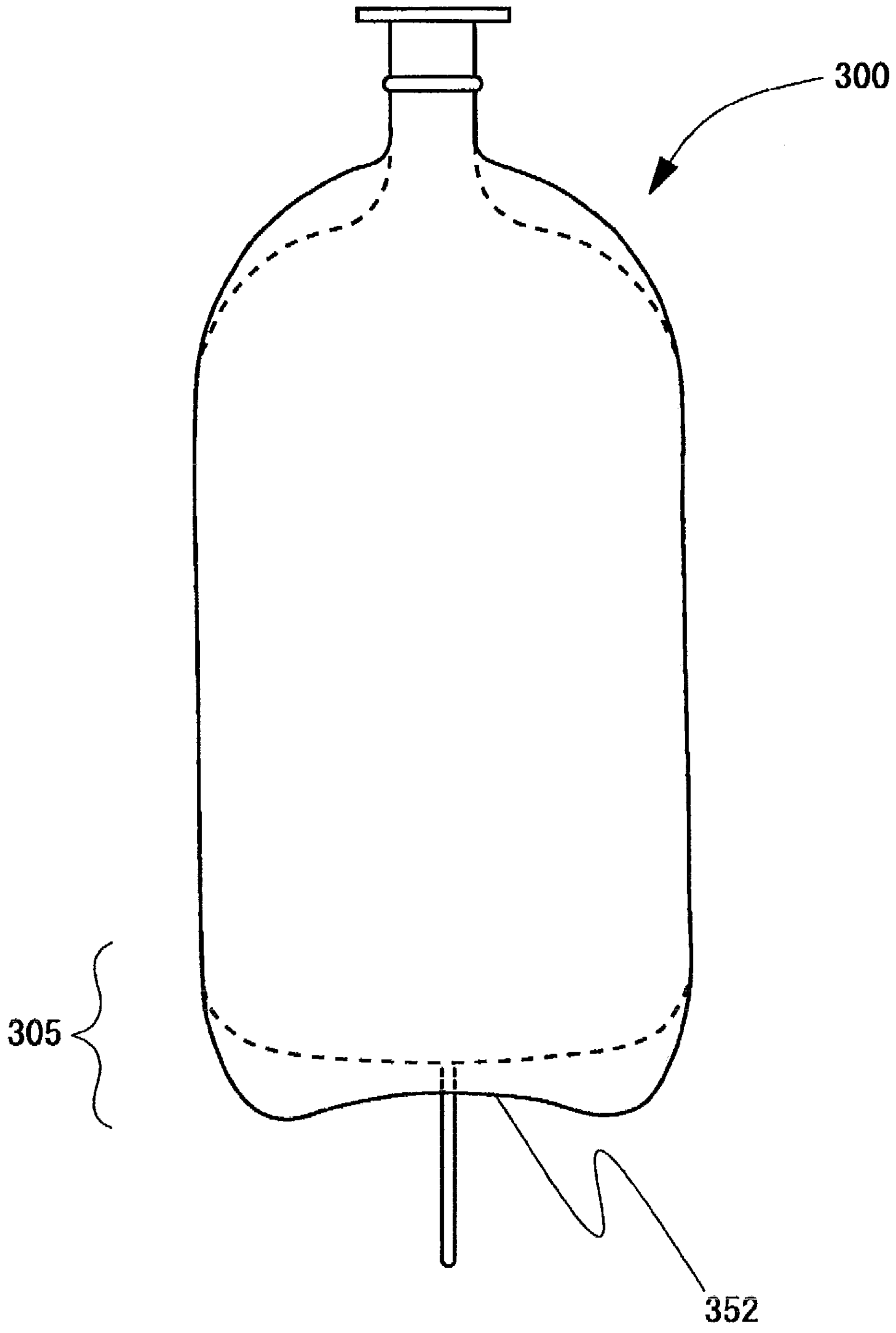
FIG. 19 is a front view of an infusion container illustrating example 7 of the present invention.
Figure 20:
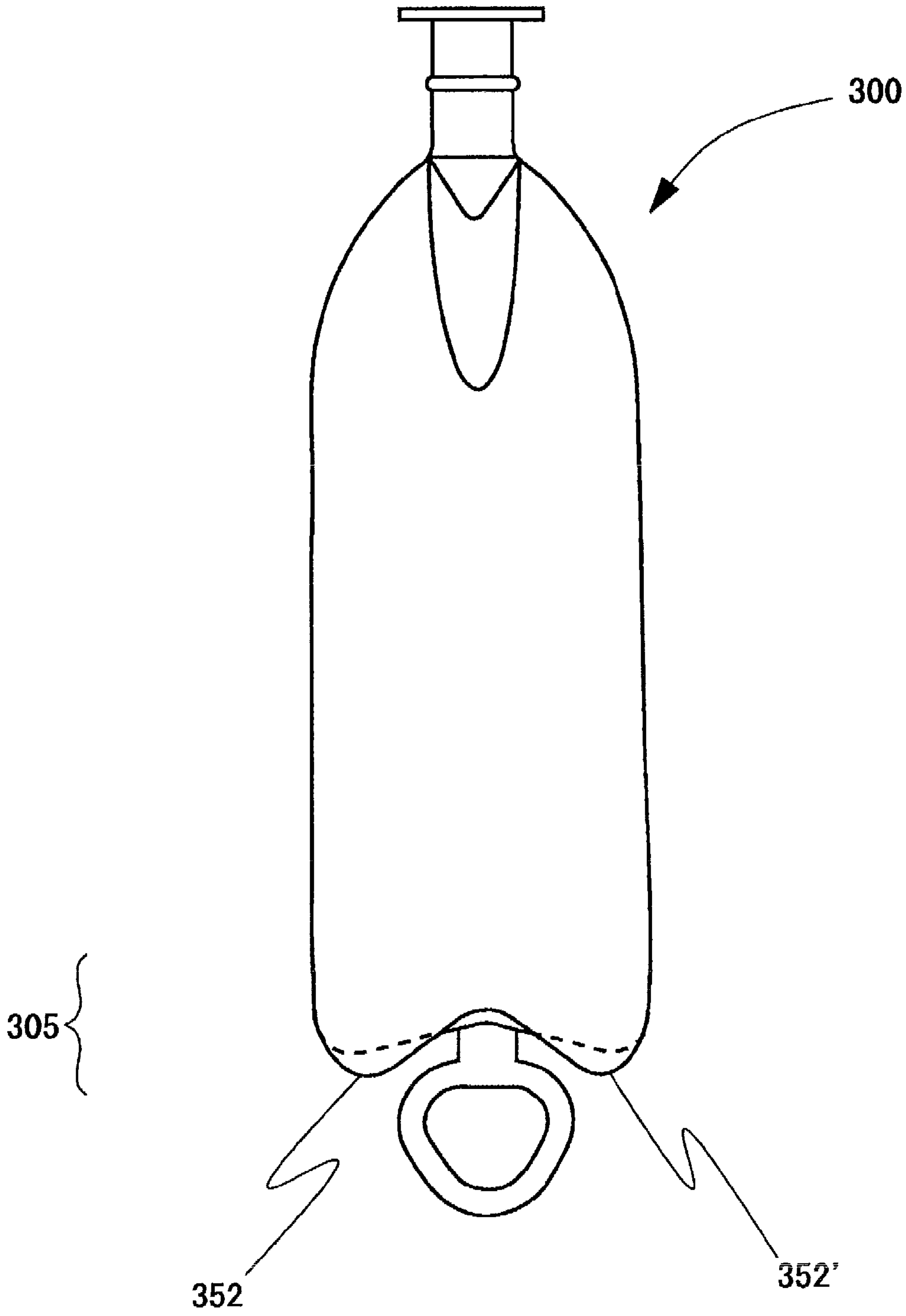
FIG. 20 is a side view of the container shown in FIG. 19.

As shown in FIGS. 19 and 20, the infusion container of example 7 differs from that of example 5 in that edge lines 252 located at the grounding portion of the bottom are formed into not straight lines extending in parallel with the long axis of the bottom in the direction of the long axis of the bottom, but curved lines slightly concaved in the direction of the mouth.

Experiments 1-4

Experiments 9

For each of examples 1-4 and comparative example 1, there were prepared five blow-molded bottles with the specification (capacity: 540 mL, weight: 12 g, minimum wall thickness: 0.15 mm) as shown in Table 1, by using a plastic material prepared by blending linear low-density polyethylene resin ("MORETEC" (Trademark) 3500Z made by Prime Polymer Co., Ltd.) and low-density (LD) polyethylene (LM360 made by Japan Polyethylene Corporation) in the weight ratio of 80:20. Each bottle was filled with 520 mL of tap water, connected to an infusion set (ISA-300A00 made by NIPRO CORPORATION) and then subjected to drainage tests by gravity fall (head drop 80 cm). The volume of water remained in each bottle was measured by 30 mL syringe to calculate the mean value of the residual liquid. Results obtained are shown in Table 2.

As can be seen from Table 2, the respective volumes of residual water in the infusion containers of examples 1 and 4 were not more than 20 mL, while the volumes of residual water in the infusion containers of examples 2 and 3 were 25 mL and 32 mL, respectively. Thus, the infusion containers of examples 1-4 are much improved in residual liquid volume as compared with the conventional infusion container of comparative example 1 (residual liquid volume: 53 mL). Thus, it can be seen that the infusion container make it possible to considerably reduce the residual liquid volume by providing the container with the bottom formed into a V-shape which is bent inwardly and symmetrically with respect to the long axis of the bottom.

Also it can be seen that the infusion container can be reduced in residual liquid by forming the shoulder into a configuration with V-shaped grooves bent inwardly and symmetrically with respect to the long axis of the bottom. In addition, it can be seen that the infusion container can be further reduced in residual liquid by respectively providing the curved portions of both the bottom and the shoulder with inwardly-foldable fold lines and by providing the narrow sidewalls of the barrel with fold lines foldable outwardly and symmetrically with respect to the longitudinal axis.

Experiments 5 and 7

Using a plastic material prepared by blending linear low-density polyethylene resin ("MORETEC" (Trademark)

3500Z made by Prime Polymer Co., Ltd.) and low-density (LD) polyethylene (LM360 made by Japan Polyethylene Corporation) in the weight ratio of 80:20, there were prepared three blow-molded bottles with the specification (capacity: 550 mL, weight: 13.7 g, minimum wall thickness: 0.16 mm) for each of examples 5, 7 shown in Table 1. The bottles were respectively filled with 520 mL of normal saline solution and 30 mL of air, sterilized by steam at 108° C. for 30 minutes after sealing, remove the air in the interior of the bottle with a syringe, connected to an infusion set (ISA-300A00 made by NIPRO CORPORATION) and then subjected to drainage by gravity fall (a gap from the port of the bottle to an intravenous infusion needle is 80 cm). After completing the drainage, the residual volume of liquid remained in the bottle was measured by a 50 mL syringe to determine the mean value of the residual liquid. Results obtained are shown in Table 3.

From Table 3, it can be seen that the drainage property for the bottle of example 5 is decreased by about 30% after being subjected to the steam sterilization, but the residual volume of liquid is 29 mL, which demonstrates that the bottle of example 5 is considerably reduced in residual volume as compared with the bottle of example 7 (the residual volume is 42 mL). Thus, it is determined that the residual volume of the liquid can be considerably reduced by providing the grounding portion with edge lines which are parallel to the long axis of the bottom and linearly extend in the direction of the long axis of bottom.

Experiment 6

In example 5, the containers were formed into a configuration shown in FIGS. 17 and 18 and having a weight of 14.7 g and a capacity increased by 50 mL compared to the container of example 5. For each of the containers, a residual volume was measured in the same manner as in example 5 before and after sterilization. Results are shown in Table 3. The bottles of example 6 showed good results since the container even after being sterilized has the residual volume of 22 mL which is not more than half of the bottle of comparative example 1.

Experiment 8

In example 5, polypropylene resin (flexural modulus: 300 MPa, Trade name: Zelas MC700, made by Mitsubishi Chemical Corporation) was used instead of plastic resin prepared by blending linear low-density polyethylene resin and low-density polyethylene in the weight ratio of 80:20, to prepare containers having a weight of 16 g and a capacity increased by 50 mL compared to the container of example 5. For the resultant containers, measurements were made on the residual volume before and after sterilization of the container in the same manner as example 5. Results are shown in Table 3. The bottles of example 8 showed good results since the infusion bottles even after sterilization have the residual volume of 24 mL which is not more than half of the conventional infusion bottle of comparative example 1.

TABLE 1

Figure 11:
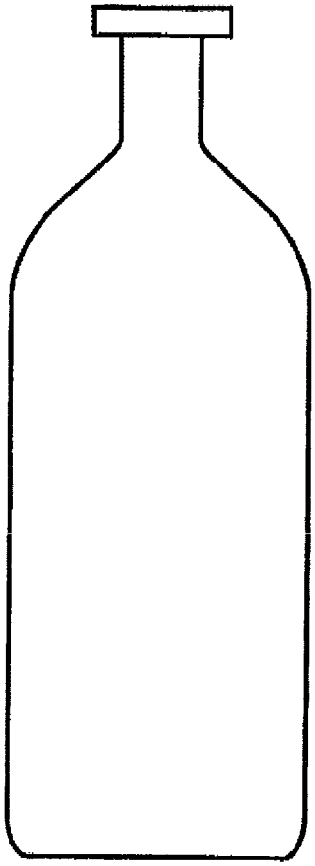
FIG. 11 is a side view illustrating a conventional bottle.

| | Kind of container | specification of container |
|---|---|---|
| Experiment 1 | Example 1 | V-shaped curved portions of bottom and shoulder, fold lines located at curved portions at bottom and shoulder, fold lines at narrow sidewalls of barrel |
| Experiment 2 | Example 2 | V-shaped curved portions of bottom, fold lines at curved portions at bottom, fold lines at narrow sidewalls of shoulder and barrel |
| Experiment 3 | Example 3 | V-shaped curved portions of bottom |
| Experiment 4 | Example 4 | V-shaped curved portions of bottom and shoulder |
| Experiment 5 | Example 5 | V-shaped curved portions of bottom and shoulder, ridge-like portions at contact area of the bottom are parallel to the long axis of the bottom and extend linearly in the direction of the long axis of the bottom. capacity: 550 cubic centimeter, weight: 13.7 g |
| Experiment 6 | Example 6 | FIG. 17, the ridge-like lines located at the top portions of the shoulder in the container of example 5 are parallel to the long axis and extend linearly in the direction of long axis. Capacity: 600 cubic centimeter, whole weight: 14.7 g |
| Experiment 7 | Example 7 | FIG. 19, edge lines 352 located at the grounding portion of the bottom are slightly curved in the direction of mouth. |
| Experiment 8 | Example 6 | made by polypropylene resin (flexural modulus: 300 MPa) |
| Experiment 9 | Comparative Example 1 | Conventional bottle (FIG. 11) |

TABLE 2

| | Exp. 1 | Exp. 2 | Exp. 3 | Exp. 4 | Exp. 9 |
|---|---|---|---|---|---|
| RV (mL) | 12 | 25 | 32 | 18 | 53 |

TABLE 3

| | Exp. 5 sterilized | Exp. 5 not sterilized | Exp. 6 sterilized | Exp. 6 not sterilized | Exp. 7 sterilized | Exp. 7 not sterilized | Exp. 8 Sterilized | Exp. 8 not sterilized |
|---|---|---|---|---|---|---|---|---|
| RV (mL) | 29 | 22 | 22 | 19 | 42 | 29 | 25 | 24 |

Exp. = Experiment

RV = residual volume

The invention claimed is:

1. A blow-molded plastic infusion container comprising:

a mouth;

a neck having a first end and a second end, the first end being connected to the mouth;

a shoulder extending downward and outward from the second end of the neck;

a barrel connected to the shoulder; and a bottom, having a hanging member, wherein said barrel has a pair of wide sidewalls and a pair of narrow sidewalls, and said bottom is formed into a V-shape bent inwardly and symmetrically with respect to the long axis of the bottom, wherein the shoulder has a pair of wide sidewalls and a pair of narrow sidewalls, said narrow sidewalls of the shoulder being provided with V-shaped groove portions bent inwardly and symmetrically with respect to the long axis, wherein the V-shaped groove portions provided on the narrow sidewalls of the shoulder extend to the second end of the neck, wherein the blow-molded plastic infusion container is structurally configured to be thinned and flattened by the discharge of infusion contained in the blow-molded plastic infusion container, and wherein the bottom and shoulder are provided at curved portions thereof with inwardly foldable fold lines.

2. The blow-molded plastic infusion container according to claim 1, wherein said narrow sidewalls of the barrel are provided with fold lines, which are outwardly foldable and symmetrical to the longitudinal axis.

3. The blow-molded plastic infusion container of claim 1, wherein edge lines in curved portions of the shoulder extend linearly in parallel with the long axis of the bottom and in the direction of the long axis.

4. The blow-molded plastic infusion container according to claim 1, wherein said narrow sidewalls of the barrel are provided with fold lines, which are outwardly foldable and symmetrical to the longitudinal axis.

5. The blow-molded plastic infusion container according to claim 3, wherein the bottom and shoulder are provided at curved portions thereof with inwardly foldable fold lines.

6. The blow-molded plastic infusion container according to claim 3, wherein said narrow sidewalls of the barrel are provided with fold lines, which are foldable outwardly and symmetrically with respect to the longitudinal axis.

7. The blow-molded plastic infusion container according to claim 1, wherein the V-shaped groove portions of the shoulder extend an entire distance from an intersection of the shoulder with the narrow sidewalls to the neck.

8. The blow-molded plastic infusion container according to claim 1, wherein the V-shaped groove portions each has a wide end and a pointed end, the wide end joins and extends from the second end of the neck, and the pointed end is positioned away from the neck toward the barrel.

9. The blow-molded plastic infusion container according to claim 1, wherein the blow-molded plastic infusion container is structurally configured to be hanged by the hanging member so that the bottom is located upside down.

10. A blow-molded plastic infusion container comprising:

a mouth;

a neck having a first end and a second end, the first end being connected to the mouth;

a shoulder extending downward and outward from the second end of the neck;

a barrel connected to the shoulder; and a bottom, having a hanging member, wherein said barrel has a pair of wide sidewalls and a pair of narrow sidewalls, and said bottom is formed into a V-shape bent inwardly and symmetrically with respect to the long axis of the bottom, wherein the shoulder has a pair of wide sidewalls and a pair of narrow sidewalls, said narrow sidewalls of the shoulder being provided with V-shaped groove portions bent inwardly and symmetrically with respect to the long axis, wherein the V-shaped groove portions provided on the narrow sidewalls of the shoulder extend to the second end of the neck, and wherein the narrow sidewalls of the shoulder includes curved portions, adjacent to the V-shaped groove portions, having a smaller thickness than that of the wide sidewalls of the shoulder.

11. The blow-molded plastic infusion container according to claim 10, wherein the bottom and shoulder are provided at curved portions thereof with inwardly foldable fold lines.

12. The blow-molded plastic infusion container according to claim 10, wherein said narrow sidewalls of the barrel are provided with fold lines, which are foldable outwardly and symmetrically with respect to the longitudinal axis.

13. The blow-molded plastic infusion container according to claim 11, wherein said narrow sidewalls of the barrel are provided with fold lines, which are foldable outwardly and symmetrically with respect to the longitudinal axis.

14. The blow-molded plastic infusion container according to claim 10, wherein the V-shaped groove portions of the shoulder extend an entire distance from an intersection of the shoulder with the narrow sidewalls to the neck.

15. The blow-molded plastic infusion container according to claim 10, wherein the V-shaped groove portions each has a wide end and a pointed end, the wide end joins and extends from the second end of the neck, and the pointy end is positioned away from the neck toward the barrel.

16. The blow-molded plastic infusion container according to claim 10, wherein the blow-molded plastic infusion container is structurally configured to be thinned and flattened by only the discharge of infusion contained in the blow-molded plastic infusion container without manually folding the container.

17. The blow-molded plastic infusion container of claim 10, wherein edge lines in curved portions of the shoulder extend linearly in parallel with the long axis of the bottom and in the direction of the long axis.

18. The blow-molded plastic infusion container according to claim 11, wherein said narrow sidewalls of the barrel are provided with fold lines, which are outwardly foldable and symmetrical to the longitudinal axis.

19. The blow-molded plastic infusion container according to claim 17, wherein the bottom and shoulder are provided at curved portions thereof with inwardly foldable fold lines.

20. A blow-molded plastic infusion container comprising:

a mouth;

a neck having a first end and a second end, the first end being connected to the mouth;

a shoulder extending downward and outward from the second end of the neck;

a barrel connected to the shoulder; and a bottom, having a hanging member, wherein said barrel has a pair of wide sidewalls and a pair of narrow sidewalls, and said bottom is formed into a V-shape bent inwardly and symmetrically with respect to the long axis of the bottom, wherein the shoulder has a pair of wide sidewalls and a pair of narrow sidewalls, said narrow sidewalls of the shoulder being provided with V-shaped groove portions bent inwardly and symmetrically with respect to the long axis, wherein the V-shaped groove portions provided on the narrow sidewalls of the shoulder extend to the second end of the neck, wherein the blow-molded plastic infusion container is structurally configured to be thinned and flattened only by the discharge of infusion contained in the blow-molded plastic infusion container without manually folding the container, and wherein edge lines in curved portions of the shoulder extend linearly in parallel with the long axis of the bottom and in the direction of the long axis.

* * * * *